US006824811B2

(12) United States Patent
Fritsche et al.

(10) Patent No.: US 6,824,811 B2
(45) Date of Patent: Nov. 30, 2004

(54) CONCENTRATE OF TRITERPENES

(75) Inventors: Jan Fritsche, Vlaardingen (NL); Otto Eduard Rosier, Spijkenisse (NL); Ulrike Schmid, Wormerveer (NL); Erik Schweitzer, Wormerveer (NL)

(73) Assignee: Loders Croklaan USA LLC, Channahon, IL (US)

( * ) Notice: Subject to any disclaimer, the term of this patent is extended or adjusted under 35 U.S.C. 154(b) by 188 days.

(21) Appl. No.: 10/118,319

(22) Filed: Apr. 9, 2002

(65) Prior Publication Data
US 2003/0049365 A1 Mar. 13, 2003

(30) Foreign Application Priority Data
Apr. 9, 2001 (EP) ............................................. 01201296

(51) Int. Cl.⁷ ............................................... A23L 1/212
(52) U.S. Cl. ....................... 426/615; 426/430; 426/489; 426/485
(58) Field of Search ................................ 426/429, 430, 426/615, 493–495, 489

(56) References Cited

U.S. PATENT DOCUMENTS

| | | | |
|---|---|---|---|
| 5,948,460 A | 9/1999 | Kang et al. | 426/548 |
| 6,123,968 A * | 9/2000 | Mendez | 426/321 |
| 2002/0019253 A1 * | 2/2002 | Cain et al. | 426/603 |

FOREIGN PATENT DOCUMENTS

| | | |
|---|---|---|
| DE | 1 152 221 | 7/1954 |
| EP | 0 555 484 A1 | 8/1993 |
| FR | 2 541 895 | 9/1984 |

OTHER PUBLICATIONS

Bock et al, "Bestandteile der aus Appeltrockentrestern Gewinnbaren Triterpenfraktion", Die Nahrung, VCH Verlagsgesellschaft, Weinheim, vol. 10, No. 5, 1966, pp. 409–412.

* cited by examiner

Primary Examiner—Carolyn Paden
(74) Attorney, Agent, or Firm—Morgan, Lewis & Bockius LLP

(57) ABSTRACT

The invention concerns concentrates of ursolic acid or its salts and oleanoic acid, wherein (i) ursolic acid and oleanoic acid or its salts are present in an total amount for the two of more than 22 wt %, preferably 30 to 65 wt %

(ii) sugar residues are present in an amount of less than 40 wt %, preferably less than 25 wt %, in particular in an amount of 1 to 10 wt %

(iii) while ursolic acid and oleanoic acid or its salts are present in a weight ratio of more than 3.6, preferably 4.0 to 6.0

(iv) the balance being other materials, including glycerides and/or triterpenes other than ursolic acid and oleanoic acid and a method to make these concentrates.

26 Claims, No Drawings

CONCENTRATE OF TRITERPENES

BACKGROUND OF THE INVENTION

1. Field of the Invention

The invention relates to concentrates of ursolic acid and oleanoic acid and their use in foods or as food supplements.

2. Description of Related Art

Ursolic acid and oleanoic acid are well known compounds that can be isolated from a number of fruit skins. A typical example of fruit skins that can be applied are apple skins, but more sources are disclosed in e.g. col.2, 1.16–20 of U.S. Pat. No. 5,948,460. In literature (cf e.g JP 09/020674 or SU 827066 or de Sousa Menezes in Anais da Bras de Cincias, Acad Brasileira de Cincias, Rio de Jan vol 70, 1998, p.761 or Bock c.s in Die Nahrung vol 10, 1966, p.409 or Croteau in Phytochem vol 8, 1969 p.219) a standard procedure for isolating ursolic acid and/or oleanoic acid from fruit skins is to perform an extraction of the skins with an organic solvent such as acetone or ethanol. However the results of the prior art techniques were found to be unsatisfactory for a number of reasons. It was found that the products obtained had a severe off taste which prevented their use in food products. Further the compounds could only be obtained in low yields, which was probably due to the presence of high amounts of unidentified organic compounds in the fruit skins, possibly being monomolecular and higher molecular sugar residues, which makes the working-up of the extraction product very difficult. Further it was found that the purity of the products obtained was far below what is considered as acceptable for use in foods while the products also had an undesired greenish colour which made them less acceptable for use in food products that should have a light or bland colour.

We therefore studied whether we could find ways to overcome above disadvantages and to come to concentrates of ursolic acid and oleanoic acid that do not display these disadvantages.

BRIEF SUMMARY OF THE INVENTION

This study resulted in the finding of novel concentrates that comprise relatively large amounts of ursolic acid and oleanoic acid or their food acceptable salts such as their alkali or alkali earth metal salts and that could be used in foods directly without the disadvantages of the known concentrates. Therefore our invention concerns in the first instance a concentrate comprising ursolic acid and oleanoic acid or their food acceptable dsalts in substantial amounts, wherein the concentrate comprises:

(i) ursolic acid and oleanoic acid or their food acceptable salts in an total amount for the two of more than 22 wt % preferably 30 to 65 wt %

(ii) sugar residues in an amount of less than 40 wt %, preferably less than 25 wt %, in particular in an amount of 1 to 10 wt %

(iii) while ursolic acid and oleanoic acid or their salts are present in a weight ratio of more than 3.6, preferably 4.0 to 6.0

(iv) the balance being other materials, including glycerides and/or triterpenes other than ursolic acid and oleanoic acid.

DETAILED DESCRIPTION OF THE INVENTION

The sugar residues can comprise mono-molecular sugars such as glucose and fructose but also di-molecular carbohydrates such as sucrose and even oligomers of carbohydrates.

Preferred products are those products wherein the other materials (iv) are present in amounts of 15 to 65 wt %, more preferably 25 to 50 wt % These other materials comprise glycerides and other triterpenes, in particular the other materials comprise 1 to 40% glycerides and for the rest other triterpenes which other terpenes comprise maslinic acid and/or pomolic acid and/or pirolonic acid Food products containing the novel concentrates are also part of the invention and thus the invention also covers food products comprising an effective amount of the concentrate as described above so that the food product can deliver by a normal daily consumption of the food product 10 to 100% of the recommended daily amount of ursolic acid and oleanoic acid. Recommended daily amounts can range from 10 mg to 4 gram per kilogram human body weight depending on the type of deficiency that is intended to be treated with the use of the food product cq health component. The effective amount being that amount that displays a noticeable effect of the consumption of the health component.

The novel concentrates can also be used in the form of food supplements and therefore our invention also concerns food supplements comprising the concentrate according to the invention in encapsulated form. The concentrates can be encapsulated in food grade or food acceptable materials, in particular the encapsulating material used herefore is selected from the group consisting of sugars, starches, modified starches, hydrocolloids, gums and gelatin In order to enable an economic and feasable route to isolate an useful concentrate of ursolic acid and oleanoic acid from natural waste materials we developed a new process. This process led to higher yields of the desired active components (ursolic acid and oleanoic acid present in this waste material) while simultaneously these active components were obtained in purer form than achievable so far. Thus according to another embodiment of our invention our invention also concerns a method for producing a concentrate with the composition according to the invention by:

(i) selecting a natural material comprising ursolic acid and oleanoic acid in sufficient amounts (ii) drying to a water level of less than 10 wt % of either
a) the natural material of step (i) or
b) milled or ground wet material of step (iii a)

(iii) milling or grinding of either
a) the wet natural material of step (i) or
b) the dried natural material of step (ii a), (iv) extracting of either
a) the milled or ground material resulting from step (iii b) or
b) the milled or ground material from step (ii a)
with an organic solvent, preferably being acetone, ethyl acetate or ethanol and collecting an extract of the final concentrate in the solvent (v) removing the solvent from the extract obtained after step (iv a) or step (iv b).

In those instances wherein the food acceptable salts are desired the above extract can be treated with a base and the salts can be isolated.

Although above process already resulted in better products and higher yields we found that these products and yields could be further improved if step (ii) or step (iii) is either preceeded or followed by a wash with an aqueous solution, followed in case a wet product is obtained by a drying, which aqueous solution preferably is applied in a weight ratio between aqueous solution and natural material of more than 2 to 1, preferably 5:1 to 30:1

Further improvements were obtained if the aqueous solution is a solution of a base and preferably has a pH of 8 to 12 or if the aqueous solution is an acidic solution, preferably with a pH=0 to 2. The best results were obtained by performing a process wherein the milling is preceeded or followed by a treatment with acid and with base (or the other way round) using an intermediate wash until about neutral. So a combined base/acid treatment is used, however the order of these treatments was found to be irrelevant.

Although many different sources of starting materials can be used in our process we found that the best results were obtained when using a cheap and easily available starting material in the form of apple skins.

We further noticed that the particle size of the products obtained after our milling or grinding step(s) also had an impact on the efficiency of our process. It was found that the best results were obtained if the milling or grinding is performed until particles are obtained with a particle size of less than 20 mm, preferably 2 to 20 mm.

Another important product parameter is the temperature during the aequous wash. It was found that the best results were obtained when using a temperature of at least 35° C., in particular at least 70° C.

The concentrates that we obtained can be used in food products for many different purposes. They e.g. can be applied in order to provide the food product with the health function known for ursolic acid resp. oleanoic acid. However we also found that these components had an impact on the crystallisation behaviour of the fat present in a food product. Therefore our invention also concerns according to a last embodiment the use of a concentrate of ursolic acid and oleanoic acid or its salts with the composition according to the invention wherein the concentrate is used to modify the crystallisation behaviour of a fat or a fat blend in a final food product to:

(i) increase the hardness of a fat blend or the final product and/or (ii) to improve the plasticity of the fat blend or final product and/or (iii) to improve the oral mouthfeel of the fat blend or the final product and/or (iv) to improve the heat resistance of the fat blend or the final product and/or (v) to improve the speed of crystallisation of the fat blend or the final product and/or (vi) to increase the aeration properties of the fat blend or the final product and/or (vii) to decrease drying times of ice cream coatings

EXAMPLES

Example 1

This example shows the benefit of a single/combined pretreatment of apple skins on the amount and purity of ursolic acid concentrate.

Skins from apples were dried in a drying cabinet at 70° C. until the residual moisture amounted <3%. From 3000 gram wet skins 900 gram dried material was collected. This material was milled in a Retch mill provided with a sieve of 1.5 mm. All material passed this sieve prior to the pretreatment. The milled skins were pretreated in various ways. The single pretreatments were:

Water,
0.05 M Na2CO3,
0.1N HCL,
0.2M H3PO4

The combined pretreatment was:
0.2M H3PO4 followed by 0.05M Na2CO3

Single Pretreatment 90 gram dried and milled apple skins were suspended in 1800 g demineralized water. The mixture was poured in a double walled vessel of 2 l provided with stirrer and thermometer. The stirrer was set at 500 rpm, the temperature within the vessel was held at 98° C. After 8 h at 98° C. the suspension was cooled to 30° C. and collected in two centrifugal flasks. The suspension was centrifuged at 3000 rpm for 15 minutes. The clear upper layer was decanted and discarded, the sediment was spreaded on dishes and dried in a drying cabinet at 70° C. until the residual moisture amounted <3%. The dried pretreated skins were milled in a Retch mill provided with a sieve of 1.5 mm.

Instead of demineralized water also pretreatments were carried out with acidic or alkaline solutions. The conditions were:

1710 ml 0.1M HCL 6h at 98° C.
1710 ml 0.05M Na2CO3 4h at 98° C.
1710 ml 0.2M H3PO4 6h at 98° C.

Combined Pretreatment

Additionally to the single pretreatment with 0.2M H3PO4, a second pretreatment was carried out with 0.05M Na2CO3. For that purpose 90 gram dried and milled apple skins was suspend in 1686 ml demineralized water and 24 ml H3PO4 (85%). The mixture was poured in a double walled vessel of 2 l provided with stirrer and thermometer. The stirrer was set at 500 rpm, the temperature within the vessel was held at 98° C. After 6 h at 98° C. the suspension was cooled to 30° C. and collected in two centrifugal flasks. The suspension was centrifuged at 3000 rpm for 15 minutes. The clear upper layer was decanted and discarded, the sediment was spreaded on dishes and dried in a drying cabinet at 70° C. until the residual moisture amounted <3%. The dried pretreated skins were milled in a Retch mill provided with a sieve of 1.5 mm.

Phosphoric acid treated skins were subjected to an additional treatment with 0.05M Na2CO3. 40 g of this material was suspended in 760 g demineralized water and the pH was adjusted to 7.0 with concentrated sodium hydroxide. 4 g Na2CO3 was added and dissolved. The suspension was stirred at 500 rpm at 98° C. for 4 h. The suspension was centrifuged at 3000 rpm for 15 minutes. The clear upper layer was decanted and discarded, the sediment was spreaded on dishes and dried in a drying cabinet at 70° C. until the residual moisture amounted <3%. The dried pretreated skins were milled in a Retch mill provided with a sieve of 1.5 mm.

Extraction

Approximately 18 grams of dried and milled skins (water<3%) were put in a Soxhlet extraction equipment and extracted with acetone. The extraction lasted 3 hours. During that time 18 repetitions per extraction took place. Acetone was almost completely removed by means of a vacuum rotation evaporator. The last traces of acetone were removed by putting the roundbottemflask in a water bath at 80° C. and maintaining this to a vacuum pump at 2 mbar for 1 h. The crude acetone extract was weighed and analysed by gas-chromatography.

Analyses

Crude acetone samples (powder) are first sililated with BSTFA at 70° C. for 4h, thereafter dissolved in hexane and then injected in the GC. The conditions of the GC were:

| | |
|---|---|
| Column: | CP-Sil 5 CB 10 m *0.32 mm Df = 0.12 carriergas He |
| Inj. amount: | 1 ul |
| inj. type: | cool on column sec cooling time 10 s |
| Pressure: | 30 kPa |
| Temp inj. | 80° C. temp interface 250° C. |
| ovenprog | 80° C. (2 min) – 10° C./min – 360° C. (15 min) |

Results of example 1

| | | | Composition of acetone extract (%) | | | | | |
|---|---|---|---|---|---|---|---|---|
| | amount (g) of extract from 100 g | amount triterpene acids/100 | triterpene acids | | High Mol. Weight triterp. | | | |
| sample | skins | g skins | Ursolic | Oleanoic | acids | TAGs | sugars | others |
| no pretreatment | 21.2 | 5.5 | 21.1 | 4.7 | 14.8 | 8.6 | 27.8 | 23.1 |
| water 98C | 20.2 | 7.9 | 32.1 | 7.2 | 22.2 | 10.0 | 7.5 | 21.0 |
| 0.05M Na2CO3 | 19.4 | 8.6 | 36.6 | 7.8 | 19.1 | 10.9 | 2.4 | 23.2 |
| 0.1M HCL | 28.0 | 10.9 | 31.6 | 7.4 | 16.1 | 12 | 6.6 | 26.3 |
| 0.2M H3PO4 | 29.8 | 7.8 | 21.8 | 4.3 | 11.8 | 8.8 | 4.5 | 48.8 |
| combined: 0.2M H3PO4 + 0.05M Na2CO3 | 22.4 | 10.0 | 37.1 | 7.5 | 17.6 | 12.2 | 3.0 | 22.6 |

Example 2

This example shows the benefit of milling apple skins on the extractable amount of ursolic acid.

Skins from apples were dried in a drying cabinet at 70° C. until the residual moisture amounted <3%. From 898 gram wet skins 274 gram dried material was collected. The water content amounted 2.8%. The batch dried skins was divided into four parts of each 68.5 g. A Retsch mill was applied to mill the skins. The mill has a rotor of 24 teeth and can used with or without a sieve. Each portion was milled differently using different sieves. The first sample (unmilled) was extracted as such. The second sample (crushed) was milled without a sieve. These particles have a diameter of 3–5 mm. The third sample (1.5 mm) was obtained by applying a sieve of 1.5 mm. All skins passed this sieve. The fourth sample (0.2 mm) was obtained by applying a sieve of 0.2 mm.

Extraction

Acetone extraction was carried out according to the method mentioned in example 1

Analyses

GC-FID analyses was carried out according to the method mentioned in example 1

Example 3

This example shows the results of a combined pretreatment carried out on natural apple skins with minimal processing. The benefit is shown on the amount and purity of the crude acetone extract. There are two process variants.

a: milling with water, acid and alkaline pretreatment followed by drying b: acid and alkaline pretreatment, followed by drying and milling Both process variants will be outlined.

Variant a 300 g natural apple skins were mixed with 1676 ml demineralized water and 24 ml H3PO4 (85%). The pH was 1.5. The mixture was poured in a double walled vessel of 2 l provided with stirrer and thermometer. The stirrer was set at 500 rpm, the temperature within the vessel was held at 98° C. After 6 h at 98° C. the suspension was cooled to 30° C., neutralised with concentrated NaOH to pH 7 and collected in two centrifugal flasks. The suspension was centrifuged at 3000 rpm for 15 minutes. The clear upper layer was decanted and discarded, the sediment was returned in the vessel. 1700 g water and 9.0 g Na2CO3 was added to the vessel and the mixture was stirred for 4 h at 98° C. The skins were cooled to 30° C., and collected in two centrifugal flasks and centrifuged at 3000 rpm for 15 minutes. The clear layer was discarded the sediment was spreaded on dishes and dried in a drying cabinet at 70° C. until the residual moisture amounted <3%. The dried pretreated skins were milled in a Retch mill provided with a sieve of 1.5 mm.

Variant b 300 g natural apple skins were mixed with 1676 ml demineralized water and the mixture of skins and water was

Results of example 2

| | | | Composition of acetone extract (%) | | | | | |
|---|---|---|---|---|---|---|---|---|
| | amount (g) of extract from 100 g | amount triterpene acids/ 100 g | triterpene acids | | High Mol. Weight triterp. | | | |
| sample | skins | skins | Ursolic | Oleanoic | acids | TAGs | sugars | others |
| no milling | 15.0 | 3.0 | 15.4 | 4.4 | 16.0 | 0.6 | 44.2 | 19.4 |
| crushed | 19.1 | 3.2 | 13.0 | 3.9 | 13.1 | 3.5 | 47.4 | 19.1 |
| 1.5 mm | 22.6 | 3.6 | 12.4 | 3.4 | 12.5 | 6.9 | 46.9 | 18.1 |
| 0.2 mm | 27.9 | 4.9 | 13.8 | 3.8 | 14.2 | 9.7 | 41.4 | 17.1 | milled through a colloid mill (Prestomill PM30). The mixture was poured in a double walled vessel of 2 l provided with stirrer and thermometer. 24 ml of concentrated H3PO4 (85%) was added. The stirrer was set at 500 rpm, the temperature within the vessel was held at 98° C. After 6 h at 98° C. the suspension was cooled to 30° C., neutralised with concentrated NaOH to pH 7 and collected in two centrifugal flasks. The suspension was centrifuged at 3000 rpm for 15 minutes. The clear upper layer was decanted and discarded, the sediment was returned in the vessel. 1700 g water and 9.0 g Na2CO3 was added to the vessel and the mixture was stirred for 4 h at 98° C. The skins were cooled to 30° C., and collected in two centrifugal flasks and centrifuged at 3000 rpm for 15 minutes. The clear upper layer was discarded, the sediment was spreaded on dishes and dried in a drying cabinet at 70° C. until the residual moisture amounted <3%.

Extraction

Acetone extraction was carried out according to the method mentioned in example 1

Analyses

GC-FID analyses was carried out according to the method mentioned in example 1

|  | Results of example 3 | | | | | | | |
|---|---|---|---|---|---|---|---|---|
|  |  | yield of acetone | Composition of acetone extract (%) | | | | | |
|  | amount (g) of dried skins from 300 g wet | extract from treated | triterpene acids | | High Mol. Weight | | | |
| sample | skins | skins (%) | Ursolic | Oleanoic | acids | TAGs | sugars | others |
| variant a | 35.9 | 21.0 | 38.9 | 8.0 | 16.3 | 10.0 | 0.3 | 26.5 |
| variant b | 36.4 | 17.6 | 38.7 | 8.1 | 17.0 | 7.2 | 0.6 | 28.4 |

Another effect of the alkaline pretreatment was observed with respect to the improved organoleptical properties. The alkaline treated material showed a significant lighter colour and less off-flavour.

What is claimed is:

1. Concentrate comprising ursolic acid and oleanoic acid or their derivatives in substantial amounts, wherein the concentrate comprises:
   (i) ursolic acid and oleanoic acid or food acceptable salts thereof in a total amount for the two of more than 22 wt %,
   (ii) sugar residues in an amount of less than 40 wt %,
   (iii) the weight ratio of ursolic acid to oleanoic acid or their salts being more than 3.6,
   (iv) the balance being other materials, including at least one member of the group consisting of glycerides and triterpenes other than ursolic acid and oleanoic acid.

2. Concentrate according to claim 1 wherein the other materials (iv) are present in amounts of 15 to 65 wt %.

3. Concentrate according to claim 1 wherein the other materials comprise 1 to 40% glycerides with the balance being at least one terpenes selected from the group consisting of maslinic acids, pomolic acid and pirolonic acid.

4. Food products comprising an effective amount of the concentrate according to claim 1 so that the food product can deliver by a normal daily consumption of the food product 10 to 100% of the recommended daily amount of ursolic acid and oleanoic acid.

5. A food product according to claim 4 wherein the recommended daily amount of ursolic acid and oleanoic acid is from 10 mg to 4 gram per kilogram of human body weight.

6. Food supplements comprising the concentrate according to claim 1 in encapsulated form.

7. Food supplements according to claim 6 wherein the encapsulating material is selected from the group consisting of sugars, starches, modified starches, hydrocolloids, gums and gelatin.

8. Method for producing a concentrate with the composition according to claim 1 which comprises:
   (i) selecting a natural material comprising ursolic acid and oleanoic acid in sufficient amounts
   (ii) drying to a water level of less than 10 wt % of either
      a) the natural material of step (i) or
      b) milled or ground wet material of step (iii a)
   (iii) milling or grinding of either
      a) the wet natural material of step (i) or
      b) the dried natural material of step (ii a),
   (iv) extracting of either
      a) the milled or ground material resulting from step (iii b) or
      b) the milled or ground material from step (ii a) with an organic solvent and collecting an extract of the final concentrate in the solvent
   (v) removing the solvent from the extract obtained after step (iv a) or step (iv b).

9. Method according to claim 8 wherein step (ii) or step (iii) is either preceded or followed by a wash with an aqueous solution, followed in case a wet product is obtained by a drying, which aqueous solution is applied in a weight ratio between aqueous solution and natural material of more than 2 to 1.

10. Method according to claim 9 wherein the aqueous solution is a solution of a base which has a pH of 8 to 12.

11. Method according to claim 9 wherein the aqueous solution is an acidic solution.

12. Method according to claim 11 wherein the aqueous acidic solution has a pH of 0 to 2.

13. Method according to claim 9 wherein said weight ratio is 5:1 to 30:1.

14. Method according to claim 8 wherein the milling or grinding is preceded or followed by a treatment with acid and with base using an intermediate wash until about neutral.

15. Method according to claim 8 wherein the natural material is washed with an organic solvent prior to subjecting it to any of steps (ii) or (iii) of said method.

16. Method according to claim 15 wherein the organic solvent is acetone, ethyl acetate or ethanol.

17. Method according to claim 8 wherein the natural material is formed by the skins of apples.

18. Method according to claim 8 wherein the milling or grinding is performed until particles with a particle size of less than 20 mm are obtained.

19. Method according to claim 18 wherein the milling or grinding is performed until particles having a particle size of 2 to 20 mm are obtained.

20. Method according to claim 6 wherein the wash with the aqueous solution is performed at a temperature of at least 35° C.

21. Method according to claim 20 wherein the wash is performed at a temperature of at least 70° C.

22. Method according to claim 8 wherein the organic solvent in (iv) is acetone, ethyl acetate or ethanol.

23. In a method wherein ursolic acid and oleanoic acid are administered to a human for improved health purposes, the improvement wherein the acids are administered as a food product comprising a concentrate according to claim 1 in an amount to provide a daily consumption amount which is 10 to 100% of the recommended daily amount for said acids, said recommended daily amount being 10 mg to 4 gram per kilogram of body weight.

24. Concentrate according to claim 1 wherein the total amount of the ursolic acid and oleanoic acid, or salts thereof, is 30 to 65 wt % of said composition; the sugar residues are less than 25 wt %; and the ursolic acid and oleanoic acid, or salts thereof, are present in a weight ratio of 4.0 to 6.0.

25. Concentrate according to claim 24 wherein the sugar residues are present in the amount of 1 to 10 wt % of said concentrate.

26. Concentrate according to claim 25 wherein the other materials (iv) are present in an amount of 25 to 50 wt % of said concentrate.

* * * * *